United States Patent [19]

Au et al.

[11] 4,453,016

[45] Jun. 5, 1984

[54] PREPARATION OF AROMATIC ALDEHYDES

[75] Inventors: Andrew T. Au, Needham; Chu W. Jung, Arlington, both of Mass.

[73] Assignee: The Dow Chemical Company, Midland, Mich.

[21] Appl. No.: 415,079

[22] Filed: Sep. 7, 1982

[51] Int. Cl.³ ............................................. C07C 45/36
[52] U.S. Cl. ................................................. 568/432
[58] Field of Search ....................................... 568/432

[56] References Cited

FOREIGN PATENT DOCUMENTS 12939 7/1980 European Pat. Off. ............ 568/432

*Primary Examiner*—Bernard Helfin
*Attorney, Agent, or Firm*—Douglas N. Deline

[57] ABSTRACT

Aromatic aldehydes are formed by the liquid phase reaction of molecular oxygen with methyl-substituted aromatic compounds in the presence of base, a cobalt, manganese, chromium or nickel salt catalyst and activated charcoal.

9 Claims, No Drawings

PREPARATION OF AROMATIC ALDEHYDES

BACKGROUND OF THE INVENTION

The present invention relates to an improved process for the oxidation of methyl-substituted aromatic compounds. More particularly, the present invention comprises an improved liquid phase catalyst system for the preparation of aromatic aldehydes, especially p-hydroxybenzaldehyde.

In U.S. Pat. No. 4,113,782, formylated phenoxy compounds are prepared by air oxidation of methylated phenoxy compounds such as p-methoxytoluene in the liquid phase in the presence of co-catalysts comprising lower fatty acids or anhydrides and at least one soluble salt of cobalt, manganese, chromium or nickel.

In E Pat. No. 12,939 to Sumitomo Chemical Company Ltd., p-cresol is oxidized in the liquid phase by an oxygen-containing gas in the presence of base and a cobalt compound or metallic cobalt.

SUMMARY OF THE INVENTION

According to the present invention, the catalytic oxidation of methyl-substituted aromatic compounds under basic conditions in the liquid phase by the action of an oxygen-containing gas in the presence of soluble cobalt, manganese, chromium or nickel salts is improved and advanced over previously known liquid phase processes by additionally adding to the system activated charcoal.

DETAILED DESCRIPTION OF THE INVENTION

Methyl-substituted aromatic compounds that are selectively oxidized according to the present invention are those previously known and taught in the art. Suitable compounds are those of the formula

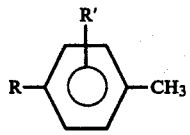

wherein R is hydroxyl or $C_{1-4}$ alkoxy, R' is halo, alkyl or hydrogen. Specific examples of suitable methyl-substituted aromatic compounds for use according to the invented process are p-cresol, 2,6-dichloro-p-cresol, 2-bromo-p-cresol, 2,4-xylenol, 3,4-xylenol, 2,6-di-tert-butyl-p-cresol, p-methoxytoluene, 2-methoxy-p-cresol, 4-methoxy-2,6-dichlorotoluene, etc.

Preferred methyl-substituted aromatic compounds are cresols, especially p-cresol, which is converted by the instant oxidation to p-hydroxybenzaldehyde. The aromatic aldehyde products of the instant process are known compounds having utility as intermediates in the preparation of pharmaceuticals, agricultural chemicals, polymeric resins and other industrial chemicals.

The process is conducted in the liquid phase. While the methyl-substituted aromatic compound may itself form the liquid phase, it is preferred to add a liquid solvent. Suitable liquids are organic compounds that are inert under the reaction conditions employed and capable of dissolving the methyl-substituted aromatic compound. Examples include alcohols, ethers, halogenated hydrocarbons, dimethylformamide, dimethylsulfoxide, etc. The solvents may be employed in combination or singly. Preferred solvents are alcohols such as methanol, ethanol, isopropanol, butanol, tertiary butanol, ethylene glycol, etc.

Bases suitably employed include alkali metal or alkaline earth metal hydroxides, alkoxides or amides. Preferred for their ready availability and low cost are sodium or potassium hydroxide. The amount of base employed is from about 1 to about 20 equivalents per equivalent of methyl-substituted aromatic compound, preferably from about 2 to about 4 equivalents.

The oxidizing agent is oxygen which may be used singly or mixed with other inert gases. Air is the preferred oxygen-containing gas. The amount or concentration of oxygen is not particularly limited and may be suitably determined by due consideration of safety and convenience. Pressures from 1 to about 100 atmospheres are suitable.

The reaction temperature is suitably from about 0° C. to about 300° C. and preferably from about 25° C. to about 100° C.

The metal salt catalysts employed are soluble salts having either organic or inorganic anions. Suitable are halide, organic acid, oxide, hydroxide or inorganic acid salts of cobalt, manganese, chromium or nickel. Initially the metal may be added in any available valence. Examples of the metal salt catalysts of the invention are fluoride, chloride, bromide, iodide, acetate, oxalate, stearate, naphthenate, nitrate, sulfate, carbonate, oxide or hydroxide salts of the above metals. Preferred catalysts are divalent or trivalent cobalt salts.

The amount of soluble metal salt employed is not critical. Suitably from about 0.001 to 1, and preferably from about 0.01 to 0.1 equivalents of metal salt per equivalent of methyl-substituted aromatic compound may be employed.

Additionally present according to the instant process is activated charcoal which is added in any suitable form, e.g., powdered, crushed or as briquets. In a continuous process, the charcoal may be present as a fixed bed or in highly comminuted form dispersed in the liquid reaction medium. The amount and type of charcoal employed is not critical. Either wood charcoal or bone charcoal or other suitable charcoal that has been activated, e.g., treated in order to increase its surface area, may be employed. The presence of activated charcoal in the invented process provides a surprising and not readily explainable improvement in the rate of oxidation of the methyl-substituted aromatic compound. Inasmuch as the metal salt oxidation catalysts are present in the homogeneous phase, the additional presence of a solid phase promotor or co-catalyst is believed to be hitherto unknown.

SPECIFIC EMBODIMENTS

Having described the invention, the following examples are provided as further illustrative and are not to be construed as limiting its scope.

EXAMPLES 1-2

In a glass flask a mixture of p-cresol (3.0 g, 0.03 mole), sodium hydroxide (3.6 g, 0.09 mole), cobalt dichloride hexahydrate (0.4 g, 0.002 mole), activated charcoal (0.2 g) and methanol (25 ml) was rapidly stirred at room temperature while oxygen was bubbled through the mixture. Samples were removed, neutralized and analyzed by gas chromatography to determine conversion to p-hydroxyaldehyde as a function of time. A second example in which activated charcoal was omitted but in all other respects the original reaction conditions were substantially identical was run for comparison purposes. Results are contained in Table I.

TABLE I

| Example | Conversion % | |
| --- | --- | --- |
| | 5 hours | 10 hours |
| 1 | 46 | 80 |
| 2 | 25 | 55 |

It may be readily seen that the additional presence of activated charcoal greatly improved the catalytic effect of the cobalt catalyst.

What is claimed is:

1. A process for preparing aromatic aldehydes comprising contacting a methyl-substituted aromatic compound corresponding to the formula:

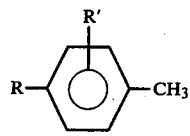

wherein R is hydroxyl or $C_{1-4}$ alkoxy, R' is halo, alkyl or hydrogen, with an oxygen-containing gas at a pressure from about 1 to about 100 atmospheres and a temperature from about 0° C. to about 300° C. in the presence of base, a metal salt catalyst selected from the salts of cobalt, manganese, chromium and nickel, and activated charcoal.

2. A process according to claim 1 wherein the metal salt catalyst is a halide, organic acid, hydroxide or inorganic acid salt.

3. A process according to claim 2 wherein the metal salt catalyst is a cobalt salt.

4. A process according to claim 1 wherein from about 0.001 to 1 equivalent of metal salt catalyst per equivalent of methyl-substituted aromatic compound is present.

5. A process according to claim 1 wherein a solvent is additionally present.

6. A process according to claim 5 wherein the solvent is an alcohol, ether, halogenated hydrocarbon, or mixture thereof.

7. A process according to claim 5 wherein the solvent is methanol.

8. A process according to claim 1 wherein the methyl-substituted aromatic compound is p-cresol and the aromatic aldehyde formed is p-hydroxybenzaldehyde.

9. A process according to claim 1 wherein the temperature is from about 25° C. to about 100° C.

* * * * *